(12) United States Patent
Zahniser et al.

(10) Patent No.: US 7,590,492 B2
(45) Date of Patent: Sep. 15, 2009

(54) METHOD AND SYSTEM FOR ORGANIZING MULTIPLE OBJECTS OF INTEREST IN FIELD OF INTEREST

(75) Inventors: David J. Zahniser, Wellesley, MA (US); Garrick L. Maenle, Columbus, OH (US); William J. Knox, Jr., West Jefferson, OH (US); Ted S. Geiselman, Bolton, MA (US); Howard L. Greene, Worthington, OH (US); Matthew S. Zelinski, Worthington, OH (US); Joseph E. Zambanini, Delaware, OH (US)

(73) Assignee: CYTYC Corporation, Marlborough, MA (US)

( * ) Notice: Subject to any disclaimer, the term of this patent is extended or adjusted under 35 U.S.C. 154(b) by 666 days.

(21) Appl. No.: 10/866,397

(22) Filed: Jun. 10, 2004

(65) Prior Publication Data

US 2004/0254738 A1 Dec. 16, 2004

Related U.S. Application Data

(60) Provisional application No. 60/478,431, filed on Jun. 12, 2003.

(51) Int. Cl.
*G01N 33/48* (2006.01)
(52) U.S. Cl. ...................................................... 702/19
(58) Field of Classification Search ................ 702/19
See application file for complete search history.

(56) References Cited

U.S. PATENT DOCUMENTS 4,513,438 A * 4/1985 Graham et al. .............. 382/134
6,252,979 B1 * 6/2001 Lee et al. .................... 382/133

FOREIGN PATENT DOCUMENTS

WO WO 02/37158 5/2002

OTHER PUBLICATIONS

Communication Pursuant to Article 94(3) EPC dated Apr. 8, 2008, for EP Application No. 04 776 235.6-2204, Applicant Cytyc Corporation (3 pages).
Examiner's Invitation to Respond to Written Opinion dated Jul. 13, 2007, for Singapore Patent Application No. 200507722-7, applicant Cytyc Corporation (5 pages).
Response to Examiner's Written Opinion dated Jul. 13, 2007, submitted Dec. 6, 2007 for Singapore Patent Application No. 200507722-7, Applicant Cytyc Corporation (3 pages).
Examination Report dated Mar. 24, 2008 for Singapore Patent Application No. 200507722-7, Applicant Cytyc Corporation (5 pages).
PCT International Preliminary Report on Patentability and Written Opinion for PCT/US2004/017414, Applicant Cytyc Corporation, Forms PCT/IB/326, PCT/IB/373 and PCT/ISA/237 dated Dec. 29, 2005 (7 pages).

* cited by examiner

*Primary Examiner*—Jerry Lin
(74) *Attorney, Agent, or Firm*—Vista IP Law Group LLP

(57) ABSTRACT

Methods, systems, and computer software for screening and assisting in screening biological specimens. Images of a biological specimen are obtained, and image data is generated from the images. Objects of interest (OOI) are identified from the image data. The OOIs are assigned to each of a plurality of fields of interest (FOIs), at least partially based on the assignment of OOIs to other FOIs. For example, OOIs that have not previously been assigned to other FOIs can be assigned to a selected FOI. In this manner, the OOIs can be grouped within the FOIs to maximize the number of OOIs included within FOIs, or alternatively, to minimize the number of FOIs required to include all of the OOIs. Once assignment of the OOIs is complete, a field of view (FOV) can be scanned relative to each FOI in order to present the OOIs to a technician, such as a cytotechnologist.

30 Claims, 6 Drawing Sheets

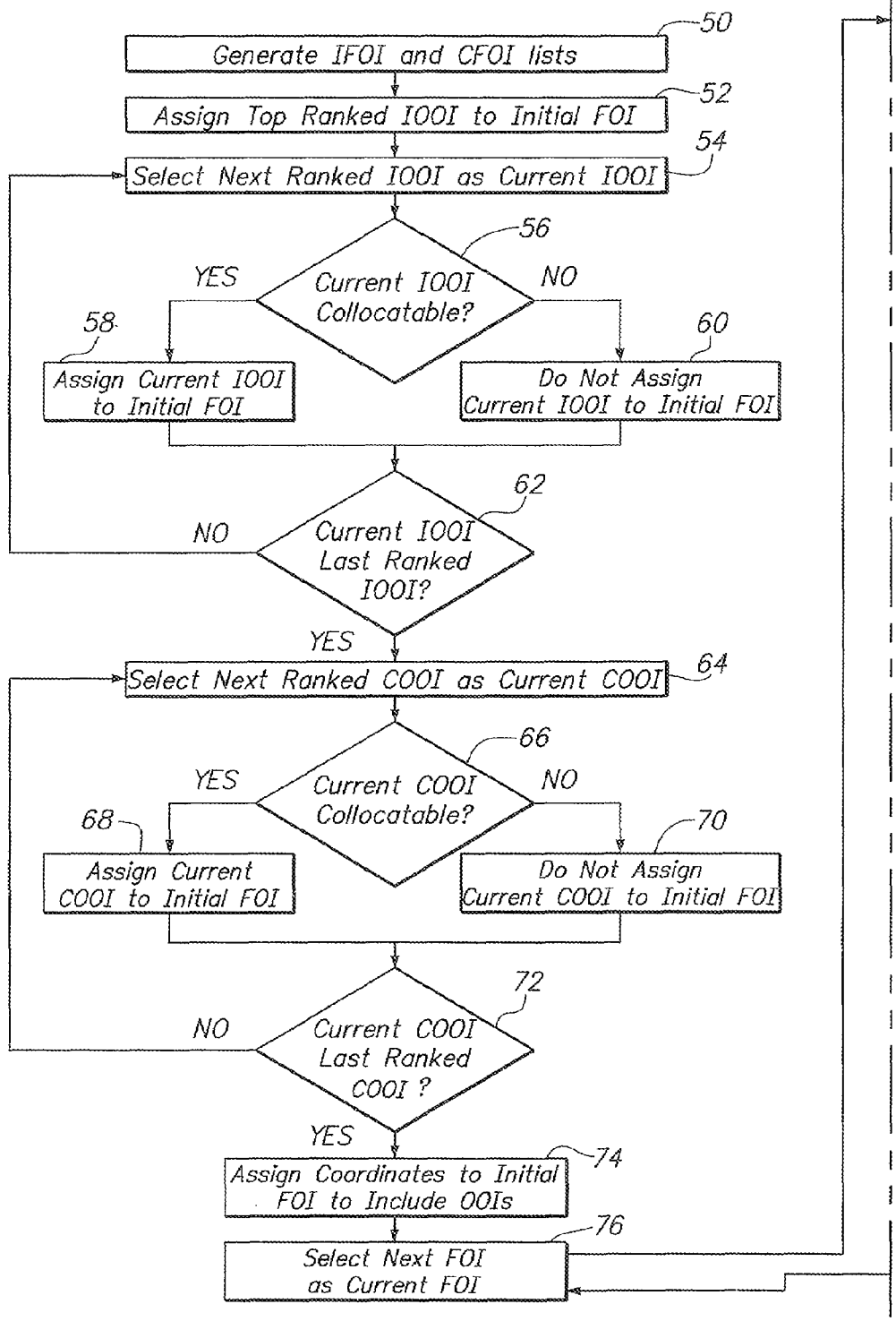

METHOD AND SYSTEM FOR ORGANIZING MULTIPLE OBJECTS OF INTEREST IN FIELD OF INTEREST

RELATED APPLICATIONS

This application claims priority from provisional U.S. Patent Application Ser. No. 60/478,431, filed Jun. 12, 2003.

FIELD OF THE INVENTION

The field of the present invention generally relates to methods and systems for analyzing cytological specimens, and more particularly to methods and system for organizing cellular material within a field of interest for display to a cytotechnologist.

BACKGROUND OF THE INVENTION

In the medical industry, there is often a need for a laboratory technician, e.g., a cytotechnologist, to review a cytological specimen for the presence of specified cell types. For example, there is presently a need to review a cervico-vaginal Papanicolaou (Pap) smear slides for the presence of malignant or pre-malignant cells. Since its introduction over fifty years ago, Pap smears have been a powerful tool for detecting cancerous and precancerous cervical lesions. During that time, the Pap smear has been credited with reducing mortality from cervical cancer by as much as 70%. This once precipitous drop in the death rate has slowed however, and the mortality rate in the United States for this preventable disease has remained virtually constant, at about 5,000 per year since the mid-eighties. Therefore, about one-third of the 15,000 women diagnosed with cervical cancer annually still die, because the cancer was detected too late. A further cause for concern is National Cancer Institute data that shows an annual 3% increase in the incidence of invasive cervical cancer in white women under 50 years of age since 1986.

A number of factors may be contributing to this current threshold, not the least of which is the fact that many women, particularly in high risk populations, are still not participating in routine cervical cancer screening. Another contributing factor that has received much attention is the limitation of the traditional Pap smear method itself.

The reliability and efficacy of a cervical screening method is measured by its ability to diagnose precancerous lesions (sensitivity) while at the same time avoiding false positive diagnosis (specificity). In turn, these criteria are dependent on the accuracy of the cytological interpretation. The conventional Pap smear has false negative rates ranging from 10-50%. This is due in large part to the vast number of cells and objects (typically as many as 100,000 to 200,000) that must be reviewed by a technician to determine the possible existence of a small number of malignant or pre-malignant cells. Thus, Pap smear tests, as well as other tests requiring detailed review of biological material, have suffered from a high false negative rate due to fatigue imposed on the technician.

To facilitate this review process, automated systems have been developed to focus the technician's attention on the most pertinent cells, with a potential to discard the remaining cells from further review. A typical automated system includes an imager and an automated optical microscope. Briefly, the imager can be operated to provide a series of numerous images of a cytological specimen slide, each depicting a different portion of the slide. The imager then processes these images to determine the most pertinent biological objects for review on the slide, and their locations (x-y coordinates) on the slide. This information is then passed onto the microscope, which automatically proceeds to the x-y coordinates and centers on the biological objects for review by the technician. During this review process, the microscope will sequentially step through the x-y coordinates of the biological objects, placing the biological object within the center of its field of view. For example, if the number of pertinent biological objects to be reviewed equals 22, the technician will review 22 regions on the slide as the microscope automatically or semi-automatically moves the field of view to the defined x-y coordinates of the biological objects. The technician can then mark any objects on the slide that he or she believe require further review by a pathologist, for example, any objects having attributes consistent with malignant or pre-malignant cells.

In general, this automated procedure has proved to be successful, since the technician's attention is focused on a limited number of objects, obviating the need for the technician to review the vast number of objects (biological or not) on the specimen. Because the technician must typically review hundreds of slides per day, however, and thus, tens of thousands of biological objects, the technician may still be subjected to fatigue. In addition, there is also a commercial aspect that must be taken into account. The cost borne by laboratories to review cytological specimens, such as Pap smear specimens, is tied, at least in part, to the time taken for a technician to review each slide. That is, the more time it takes for a technician to review a slide, the more cost in labor the laboratory incurs. Conversely, the less time that it takes for a technician to review a slide, the more money the laboratory can save.

SUMMARY OF THE INVENTION

In accordance with one aspect of the invention, a method for presenting objects of interest (OOIs) in a biological specimen slide, such as cells and/or cell clusters, for viewing by a technician is provided. The OOIs are presented for viewing within fields of interest (FOIs) covering portions of the slide in order to optimize number of OOIs within each FOI. The FOIs may have predetermined dimensions, or dimensions that can dynamically vary.

In one preferred embodiment, the method includes obtaining images of the specimen slide, generating image data from the images, and identifying OOIs from the image data. One or more OOIs are assigned to each of a number of FOIs for viewing based, at least partially, on the assignment of OOIs to other FOIs. This involves assigning OOIs to an FOI that have not been previously assigned to other FOIs. In this manner, the OOIs can be grouped within the FOIs in a coordinated manner, so that the number of OOIs that are included within FOIs can be maximized. Alternatively, if the number of FOIs is not fixed, the number of FOIs required to include all of the OOIs can be minimized. The method further comprises automatically or semi-automatically scanning a field of view (FOV) relative to each FOI in order to present the one or more OOIs in each FOI.

In one embodiment, a subset of the total OOIs are selected for FOIs by ranking the OOIs based, for example, on physical attributes of interest. For example, if the OOIs are cells, the cells may be ranked according to their nuclear integrated or average optical density. This ranking step can be applied to any case, but particularly lends itself to the case where there is a limited number of FOIs, so that some OOIs may be left out. In this manner, ranking the OOIs helps to ensure that the highest risk cells are included in the FOIs.

Whether the OOIs are ranked or not, the preferred method of assigning previously unassigned OOIs to an FOI can be accomplished in a number of ways. For example, the method can comprise sequentially selecting OOIs that have not been assigned to any FOI. The initially selected OOI is assigned to the FOI (in effect, initializing the FOI). Each subsequently selected OOI that can be collocated with OOIs previously assigned to the FOI, is then identified as being collocatable and assigned to the FOI.

In a preferred method, coordinates are assigned to the FOI, such that it includes all of the collocatable OOIs. For example, the FOI can be centered over the initial OOI or centered over the group of collocatable OOIs. In general, the manner in which the FOI is positioned over the collocatable OOIs will affect the manner in which collocatable OOIs are identified. For example, if the FOI is centered on the initial OOIs, those OOIs simply falling within the FOI are considered collocatable. If the FOI is centered over the group of OOIs, collocatable OOIs may be identified in another manner.

For example, a boundary, which is preferably geometrically similar to the FOI (e.g., each is a two-dimensional box), may be defined to include the initially selected OOI. Then, the boundary is iteratively expanded to include each subsequently selected OOI. If the expanded boundary has a dimension that is the same or smaller than the corresponding dimension of the FOI, the subsequently selected OOI is identified as being collocatable and the expanded boundary is set as the new boundary for the next iteration. If the expanded boundary has a dimension that is greater than the corresponding dimension of the FOI, the subsequently selected OOI is identified as being non-collocatable and the expanded boundary reverts back, that is the previously boundary is set as the new boundary for the next iteration.

In the case where there are two types of OOIs (e.g., individual OOIs (IOOIs) and clustered OOIs (COOIs)), the method can preferentially assign one type of OOI to one set of FOIs, and preferentially assign the other type of OOI to a different set of FOIs. In this manner, it is ensured that each OOI type will be included within an FOI. In this case, the FOIs can be topologically divided into primary FOIs and secondary FOIs, and the OOIs can be divided into primary OOIs and secondary OOIs. One or more primary OOIs are assigned to each primary FOI, and one or more secondary OOIs are assigned to the secondary FOIs. This assignment step can be accomplished in the same manner described above. To maximize coverage of the OOIs, one or more secondary OOIs can be assigned to each primary FOI, preferably after the primary OOIs have been assigned to the primary FOI. Likewise, one or more primary OOIs can be assigned to each secondary FOI, preferably after the secondary OOIs have been assigned to the secondary FOI.

In accordance with a second aspect of the invention, a biological screening system for presenting OOIs is provided. The system comprises an imaging station for obtaining images of a specimen slide, and generating image data from the images. The system further comprises at least one processor for filtering and/or processing the image data to obtain OOIs, and for assigning one or more OOIs to each FOI, at least partially, based on the assignment of OOIs to other FOIs. Assignment of the OOIs to each FOI can be accomplished in the same manner described above. The system further comprises an automated or semi-automated microscope for scanning a field of view (FOV) relative to each FOI to present the one or more OOIs in each FOI.

BRIEF DESCRIPTION OF THE DRAWINGS

The drawings illustrate the design and utility of a preferred embodiment of the present invention, in which similar elements are referred to by common reference numerals, and in which.

DETAILED DESCRIPTION OF PREFERRED EMBODIMENTS

Figure 1:
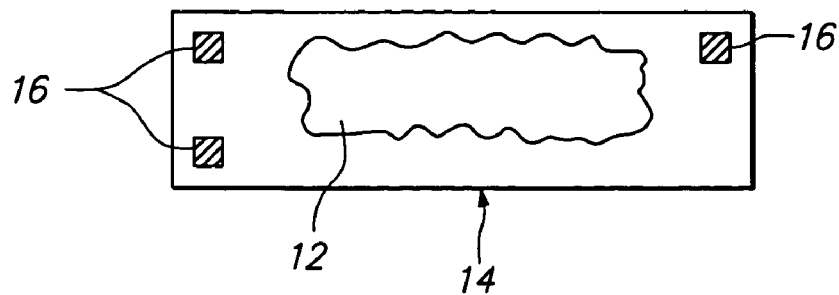
FIG. 1 is a plan view of a standard microscope slide carrying a biological specimen.
Figure 3:
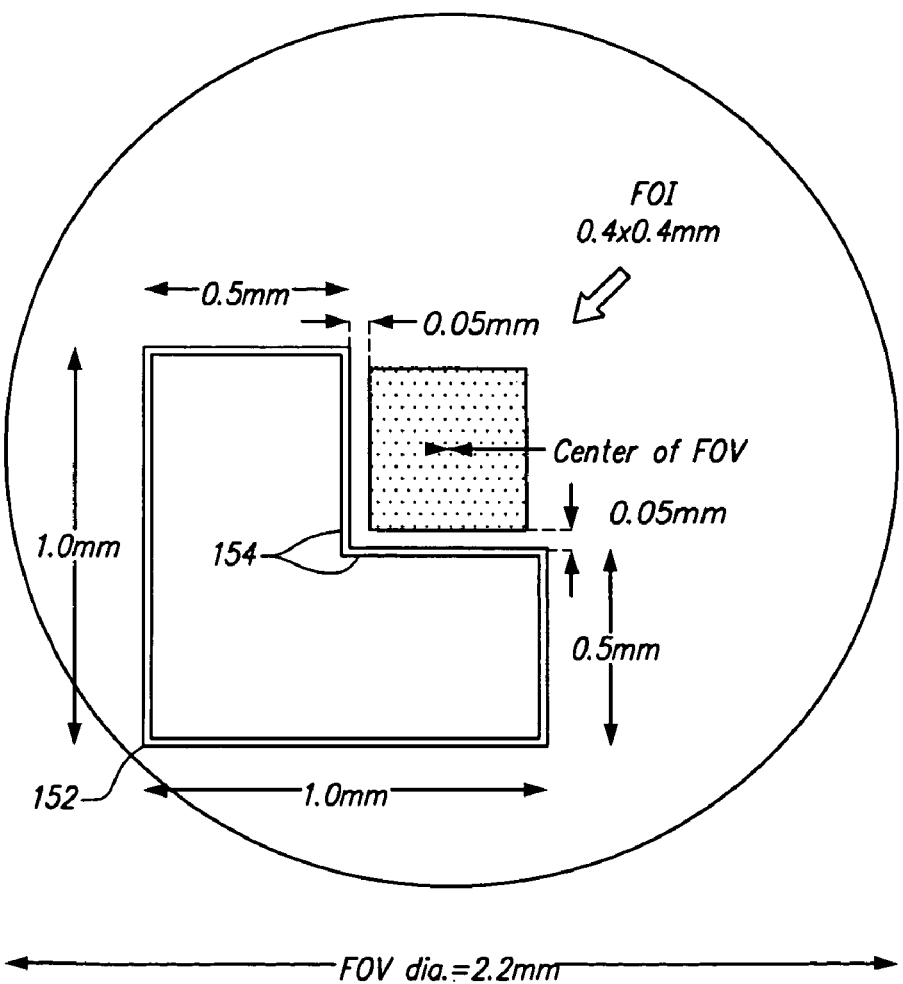
FIG. 3 is a view of a field of interest (FOI) and marker indicator as shown through a field of view (FOV) of a microscope used in the system of FIG. 2.
Figure 2:
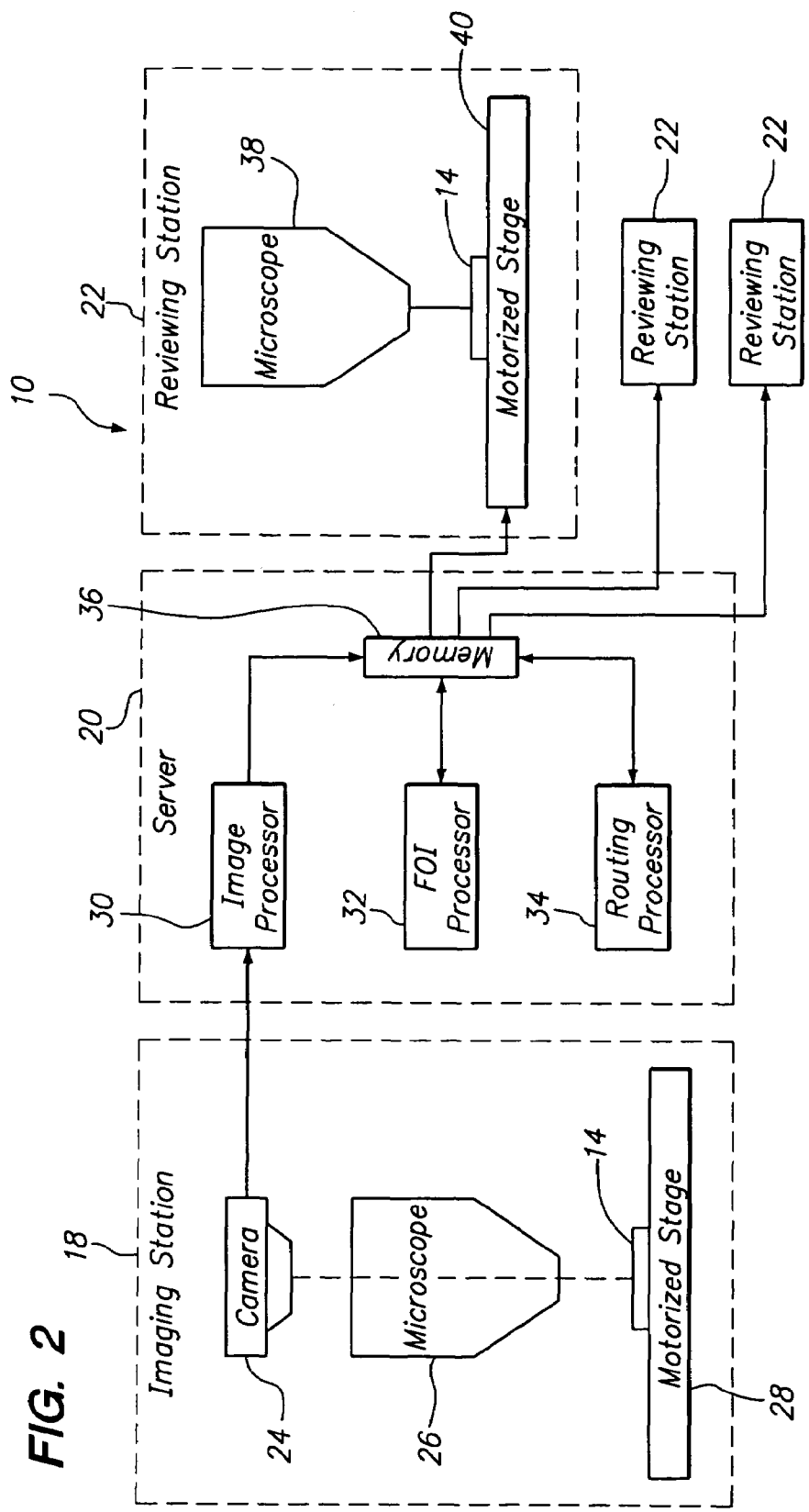
FIG. 2 is a plan view of a biological screening system constructed in accordance with one preferred embodiment of the present invention.

Referring to FIG. 2, a biological screening system 10 constructed in accordance with one preferred embodiment of the present invention is described. The system 10 is configured for presenting a biological specimen 12 located on a microscope slide 14 (best shown in FIG. 1) to a technician, such as a cytotechnologist, who can then review objects of interest (OOIs) located in the biological specimen 12. The OOIs are arranged in a number of fields of interest (FOIs) (one of which is illustrated in FIG. 3) that cover portions of the slide 14, so that the cytotechnologist's attention can be subsequently focused on OOIs within the FOIs, rather than slide regions that are not pertinent. The slide 14 is provided with fiducial marks 16, the function of which will be described in further detail below.

Although the system 10 can be used to present any biological specimen (or even a non-biological specimen, such as a computer chip) that requires further review, the system 10 lends itself particularly well to the presentation of cytological cervical or vaginal cellular material, such as that typically found on a Pap smear slide. In this case, the OOIs take the form of individual cells and cell clusters that are reviewed to check for the possible presence of an abnormal condition, such as malignancy or pre-malignancy. The biological specimen 12 will typically be placed on the slide 14 as a thin cytological layer. Preferably, a cover slip (not shown) is adhered to the specimen 12, thereby fixing the specimen 12 in position on the slide 14. The specimen 12 may be stained with any suitable stain, such as a Papanicolaou stain.

The system 10 generally comprises (1) an imaging station 18 for obtaining images of the biological material contained on the slide 14 and generating electronic image data from the images; (2) a server 20 for filtering and processing the image data to identify OOIs, and for assigning one or more of OOIs to each FOI; and (3) a plurality of reviewing stations 22 (3 shown), each of which provides a field of view (FOV) (illustrated in FIG. 3) that is scanned relative to each FOI in order to present the OOIs for viewing by a cytotechnologist. The system 10 may also comprise a user interface (not shown), including a monitor, keyboard, and mouse (all not shown), so that the cytotechnologist can interact with the system 10.

The imaging station 18 is configured to image the slide 14, which is typically contained within a cassette (not shown) along with other slides. During the imaging process, the slides are removed from the respective cassettes, imaged, and then returned to the cassettes in a serial fashion. In the illustrated embodiment, the imaging station 18 is capable of processing up to 10 cassettes, each holding up to 25 slides, in about 16 hours.

The imaging station 18 comprises a camera 24, a microscope 26, and a motorized stage 28. The camera 24 captures magnified images of the slide 14 through the microscope 26. The camera 24 may be any one of a variety of conventional cameras, such as a charge coupled device (CCD) camera, which alone or in conjunction with other components, such as an analog-to-digital (A/D) converter, can produce a digital output of sufficient resolution to allow processing of the captured images, for example a digital image having a resolution of 640×480 pixels. Preferably, each pixel is converted into an eight-bit value (0 to 255) depending on its optical transmittance, with "00000000" being the assigned value for least amount of light passing through the pixel, and "11111111" being the assigned value for a greatest amount of light passing through the pixel.

The slide 14 is mounted on the motorized stage 28, which scans the slide 14 relative to the viewing region of the microscope 26, while the camera 24 captures images over various regions of the biological specimen 12. The shutter speed of the camera 24 is preferably relatively high, so that the scanning speed and/or number of images taken can be maximized. The motorized stage 28 keeps track of the x-y coordinates of the images as they are captured by the camera 24. For example, encoders (not shown) can be coupled to the respective motors of the motorized stage 28 in order to track the net distance traveled in the x- and y-directions during imaging. These coordinates are measured relative to the fiducial marks 16 affixed to the slide 14 (shown in FIG. 1). As will be described in further detail below, these fiducial marks 16 will also be used by the reviewing station 22 to ensure that the x-y coordinates of the slide 14 during the review process can be correlated to the x-y coordinates of the slide 14 obtained during the imaging process.

Among other processing components that are not immediately pertinent to an understanding of the present invention, the server 20 comprises (1) an image processor 30 that is configured to identify OOIs from the image data acquired from the camera 24; (2) an FOI processor 32, which is configured to assign OOIs to each FOI; (3) a routing processor 34, which is configured to map routing path that the reviewing station 22 will use to scan from one FOI to the next; and (4) a memory 36 configured for storing the OOIs and FOIs, the ranking and x-y coordinates of the OOIs, and the routing path for the FOIs. It should be appreciated that the functions performed by the respective processors 30, 32, and 34 can be performed by a single processor, or alternatively, performed by more than three processors. Likewise, it can be appreciated that the memory 36 can be divided into several memories.

The image processor 30 identifies the OOIs within the biological specimen 12 by manipulating the digital images received from the camera 24 in a suitable manner. In the preferred embodiment, the image processor 30 accomplishes this using primary and secondary segmentation operations.

In the primary segmentation operation, the image processor 30 removes artifacts from further consideration. The image processor 30 accomplishes this by masking pixels in the digital image data from further consideration that, by virtue of their lightness, are unlikely to be cell nuclei. The remaining pixels in the digital image form "blobs" having all manner of shapes and sizes. The image processor 30 then performs an erosion process on the blobs in order to remove from further consideration blobs that are only a few pixels in diameter and narrow strands extending from blobs or connecting adjacent blobs. The image processor 30 then determines whether each blob in the image is an individual object or a clustered object, depending on the number of pixels in the blob. For example, a blob having more than 500 pixels might be considered a clustered object, whereas a blob having 500 or less pixels might be considered an individual object. For individual objects, blobs that do not meet certain criteria related to total area, perimeter to area ratio, optical density standard deviation, and grayscale mean pixel value are not considered further.

In the secondary segmentation operation, the image processor 30 removes blobs that are unlikely to be individual cells or clustered cells. For individual objects, the image processor 30 performs a series of erosion operations, which remove small objects and eliminates projections from the remaining blobs, and dilation operations, which remove holes from the remaining blobs. For clustered objects, the image processor 30 sharpens the edges of the object to provide a defined border. From the defined clustered object, the image processor 30 then selects an individual object or objects having the highest integrated optical density. The individual objects extracted from clusters objects will be flagged as cluster-extracted objects.

In the classification operation, the image processor 30 measures various features for each of the individual objects and clustered objects, and then calculates an object score for each object based on the measured values of these features. Based on this score, the image processor 30 removes individual objects and clustered objects that are likely to be artifacts. Those remaining are considered OOIs, with the individual objects representing individual OOIs (IOOIs), and the clustered objects representing clustered OOIs (COOIs). The image processor 30 then evaluates the OOIs for their nuclear integrated or average optical density, and ranks the OOIs in accordance with their optical density values. For each digital image, the image processor 30 stores the OOIs, along with their relative ranking and coordinates, within the memory 36 as a frame data record (FDR). In the illustrated embodiment, approximately 2000 digital images are obtained for each slide 14, and thus approximately 2000 FDRs will be stored in memory 36 for each slide 14. In the illustrated embodiment, the image processor 30 limits the number of OOIs contained in each FDR to 10 for individual OOIs and 3 for clustered OOIs.

The FOI processor 32 assigns OOIs to each FOI based on the ranking of the OOIs. Assignment of the OOIs is accomplished in a manner that avoids assignment of OOIs to an FOI that have already been assigned within another FOI. In this manner, the OOIs can be grouped within the FOIs (which in the preferred embodiment, have a fixed number) in a coordinated manner, so that the number of OOIs that are included within FOIs can be maximized. Alternatively, if the number of FOIs is not fixed, the number of FOIs required to include all of the OOIs can be minimized. In the preferred embodiment, 20 IOOI preferential FOIs and 2 COOI preferential FOIs will be generated. Thus, it can be ensured that both IOOIs and COOIs will be included within the FOIs for subsequent review by the cytotechnologist.

Figure 4:
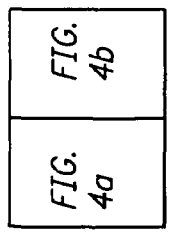
FIG. 4 is a flow diagram of process used by an FOI processor of the system of FIG. 2 to assign objects of interest (OOIs) to FOIs.
Figure 4B:
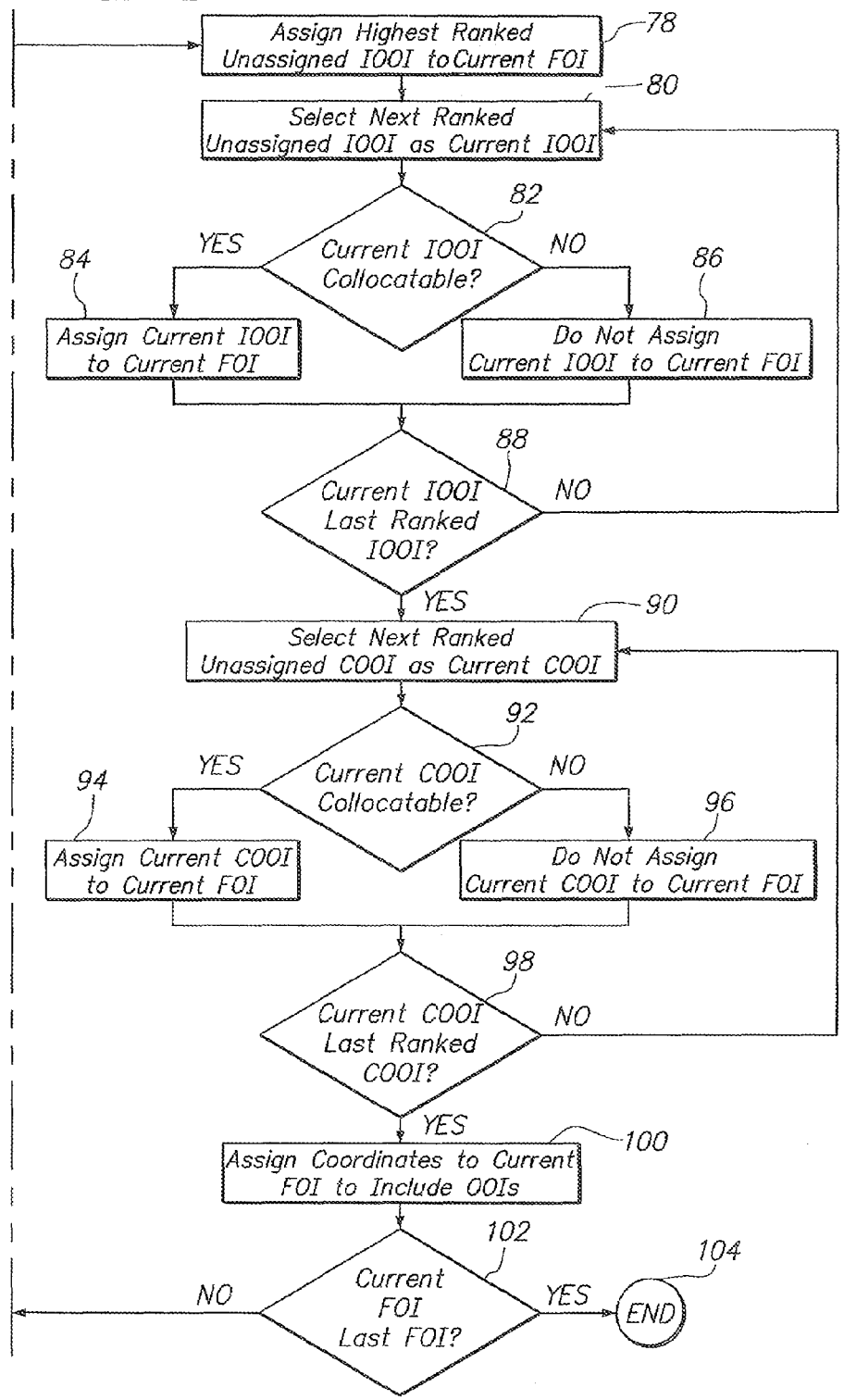
Figure 5:
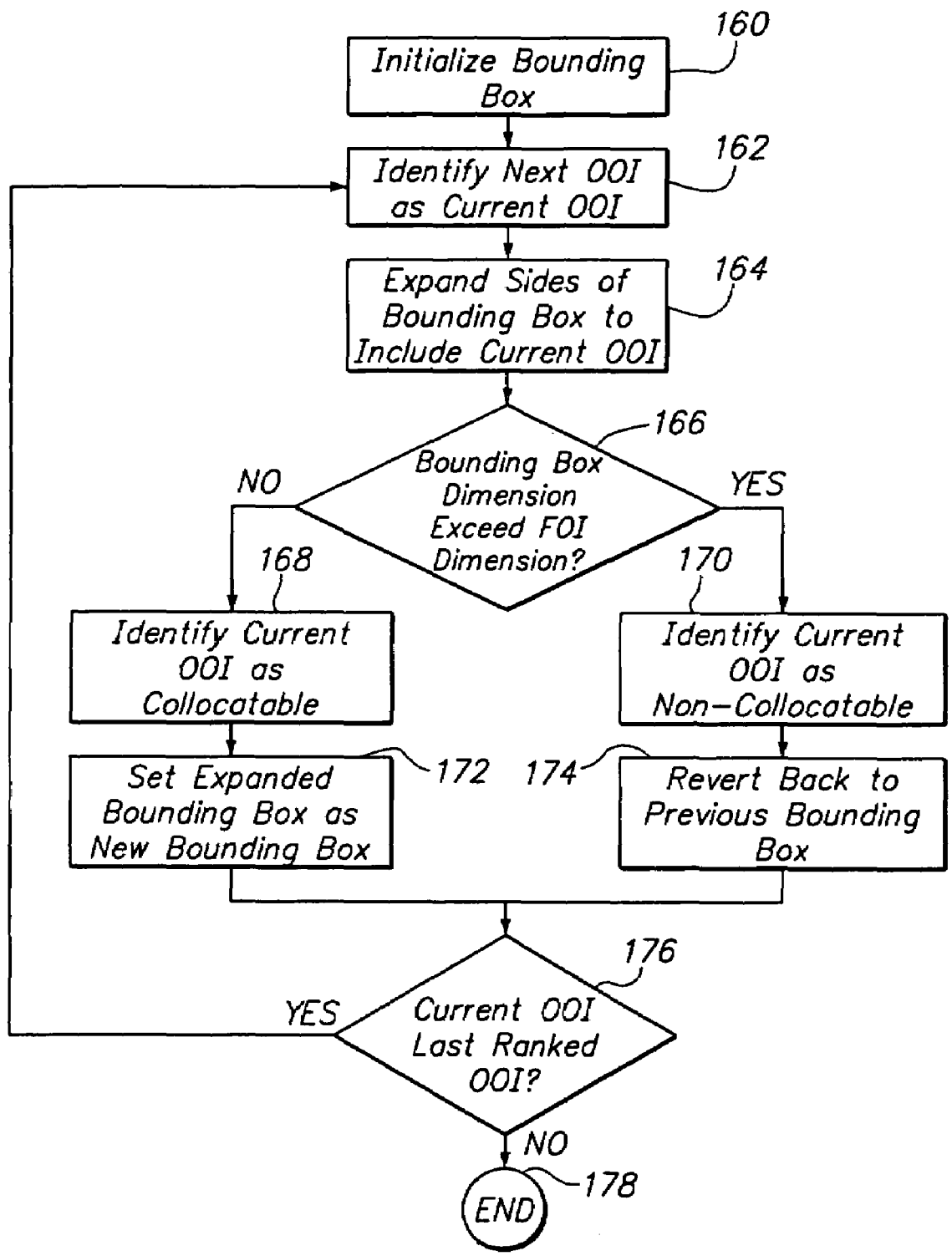
FIG. 5 is a flow diagram of one processed used by the FOI processor to determine if an OOI is collocatable with OOIs previously assigned to an FOI.

Referring now to FIG. 4, the process used by the FOI processor 32 to generate OOI preferential FOIs (in this case, 20) will be discussed in detail. First, the FOI processor 32 accesses the FDRs stored in memory 36 for the current slide 14, and extracts the IOOIs and COOIs to create an IOOI list and a COOI list (action block 50). Alternatively, the individual and clustered OOIs can be combined into a single list. The cluster-extracted IOOIs (i.e., the IOOIs that were extracted from clusters) will be flagged as such. In the preferred embodiment, the lists contain a predetermined number of OOIs, e.g., 100 IOOIs and 20 COOIs for the respective lists. In this manner, subsequent processing and human reviewing time is minimized by excluding lower risk OOIs from further consideration by the FOI processor 32 and cytotechnologist.

The FOI processor 32 then generates the FOIs, which have a predetermined size, by assigning x-y coordinates to them based on the x-y coordinates and rankings of the OOIs. Specifically, the FOI processor 32 assigns the top ranked IOOI (i.e., the first IOOI in the list) to the initial FOI (action block 52). The FOI processor 32 then selects the next ranked IOOI (in this case, the second ranked IOOI) as the current IOOI (action block 54), and determines if the current IOOI and the IOOIs previously assigned to the initial FOI can be collocated within the initial FOI (decision block 56). Notably, in the first pass, the second ranked IOOI will be the current IOOI, and the previously assigned IOOIs will only include the initial (i.e., first ranked) IOOI.

If the current IOOI can be collocated with the previously assigned IOOIs, the current IOOI is identified as a collocatable IOOI and is assigned to the initial FOI (action block 58). If the current IOOI cannot be collocated with the previously assigned IOOIs, the current IOOI is identified as a non-collocatable IOOI and is not assigned to the initial FOI (action block 60). The FOI processor 32 then determines if the current IOOI is the last ranked IOOI (decision block 62). If not, the process goes back to block 54, where the next ranked IOOI is selected as the current IOOI. Thus, it can be appreciated, that the FOI processor 32 will iterate through blocks 54-60 in order to assign all collocatable IOOIs to the initial FOI. The number of iterations will be equal to the number of IOOIs in the list minus one (i.e., minus the initial IOOI), which in this case, will be 99 times.

If the current IOOI is the last ranked IOOI, the FOI processor 32 will iterate through the COOI list in order to assign any collocatable COOIs to the initial FOI. Specifically, the FOI processor 32 selects the next ranked COOI as the current COOI (action block 64), and determines if the current COOI can be collocated with the previously assigned IOOIs and COOIs (decision block 66). Of course, if the top ranked COOI is the next ranked COOI, the FOI processor 32 need only determine if the current COOI can be collocated with the previously assigned IOOIs, since there will be no previously assigned COOIs in the initial FOI. In any event, if the current COOI can be collocated with the previously assigned IOOIs, the current COOI is identified as a collocatable IOOI and is assigned to the initial FOI (action block 68). If the current COOI cannot be collocated with the previously assigned IOOIs, the current COOI is identified as a non-collocatable IOOI and is not assigned to the initial FOI (action block 70).

The FOI processor 32 then determines if the current COOI is the last ranked COOI (decision block 72). If not, the process goes back to block 64, where the next ranked COOI is selected as the current COOI. Thus, it can be appreciated, that the FOI processor 32 will iterate through blocks 64-70 in order to assign all collocatable COOIs to the initial FOI. The number of iterations will be equal to the number of COOIs in list, which in this case, will be 20 times.

If the current COOI is the last ranked COOI, the initial FOI will be defined by assigning x-y coordinates the initial FOI in a manner that includes all of the collocatable OOIs (IOOIs and COOIs) (action block 74). As will be described in further detail below, the manner in which the x-y coordinates are assigned to the initial FOI will depend, largely in part, upon the manner in which the OOIs are determined to be collocatable.

Next, the FOI processor 32 defines the next FOI by assigning previously unassigned collocatable IOOIs to the FOI. Specifically, the FOI processor 32 selects the next FOI as the current FOI (action block 76), and assigns the highest ranked previously unassigned IOOI to the current FOI (action block 78). For example, if the first and second ranked IOOIs have previously been assigned, but the third ranked IOOI has not, the third ranked IOOI will be assigned to the current FOI. The FOI processor 32 then selects the next ranked previously unassigned IOOI as the current IOOI (action block 80). For example, if the fifth, sixth, and seventh IOOIs have previously been assigned, but the eighth ranked IOOI has not, the eighth ranked IOOI will be selected as the current IOOI.

In the same manner described above with respect to the initial FOI, the FOI processor 32 will determine if the current IOOI is collocatable with the IOOIs previously assigned to the current FOI (decision block 82). Notably, in the first pass, the previously assigned IOOIs will only include the IOOI that was initially assigned to the current FOI. If collocatable, the current IOOI will be assigned to the current FOI (action block 84), and if not, the current IOOI will not be assigned to the current FOI (action block 86). The FOI processor 32 then determines if the current IOOI is the last ranked previously unassigned IOOI (decision block 88). If not, the process goes back to action block 80, where the next ranked previously unassigned IOOI is selected as the current IOOI. Thus, it can be appreciated, that the FOI processor 32 will iterate through blocks 80-86 in order to assign all previously unassigned collocatable IOOIs to the current FOI.

If the current IOOI is the last ranked IOOI, the FOI processor 32 will iterate through the COOI list in order to assign any previously unassigned collocatable COOIs to the current FOI in the same manner described above with respect to the initial FOI. Specifically, the FOI processor 32 selects the next ranked previously unassigned COOI as the current COOI (action block 90), and determines if the current COOI can be collocated with the previously assigned IOOIs and COOIs (decision block 92). Again, if the highest ranked previously unassigned COOI is the next ranked COOI, the FOI processor 32 need only determine if the current COOI can be collocated with the previously assigned IOOIs, since there will be no previously assigned COOIs in the FOI. If collocatable, the current COOI will be assigned to the current FOI (action block 94), and if not, the current COOI will not be assigned to the current FOI (action block 96). The FOI processor 32 then determines if the current COOI is the last ranked previously unassigned COOI (decision block 98). If not, the process goes back to block 90, where the next ranked previously unassigned COOI is selected as the current COOI. Thus, it can be appreciated, that the FOI processor 32 will iterate through blocks 90-96 in order to assign all previously unassigned collocatable COOIs to the current FOI. If the current COOI is the last ranked COOI, the current FOI will be defined by assigning x-y coordinates to the current FOI in a manner that includes all of the collocatable OOIs (IOOIs and COOIs) (action block 100).

The FOI processor 32 will then determine whether the current FOI is the last IOOI preferential FOI (in this case, the $20^{th}$ FOI) (decision block 102). If not, the process returns to block 76 where the next FOI is selected as the current FOI, and then the previously unassigned collocatable IOOIs and COOIs are assigned to it.

If the current FOI is the last IOOI preferential FOI, the process ends (action block 104), and then the FOI processor 32 will generate COOI preferential FOIs (in this case, the final 2 FOIs) in a manner similar to that used to generate FOIs set out in blocks 76-100. The significant difference is that the previously unassigned collocatable COOIs will be assigned to the FOIs before the previously unassigned collocatable IOOIs are. Another difference stems from the fact that there may be less than 2 previously unassigned COOIs left after the 20 IOOI preferential FOIs are generated, and thus, at least one of the COOI preferential FOIs cannot be initialized with a COOI. In this case, the FOI processor 32 will attempt assign previously unassigned cluster-extracted IOOIs (i.e., IOOIs that have been flagged as being extracted from clusters) to the FOI(s). If there are not enough previously unassigned cluster-extracted IOOIs, the FOI processor 32 will assign previously unassigned IOOIs that were not extracted from clusters to the FOI(s).

As briefly mentioned above, the manner in which the OOIs are determined to be collocatable, and the manner in which the x-y coordinates are assigned to the FOIs are interrelated. For example, if the x-y coordinates are assigned to the FOI, such that it is centered over the initial OOI assigned to it, the FOI will be fixed in position, and OOIs falling within the borders of this fixed FOI will simply be considered collocatable, while the OOIs falling outside of the borders of the fixed FOI will simply be considered non-collocatable. If x-y coordinates are assigned to the FOI, such that it is ultimately centered over a group of OOIs, and thus is allowed to move from the initially assigned OOI, an OOI falling within the borders of the dynamically movable FOI (assuming that the FOI is moved to accommodate the OOI and the current collocatable OOIs), without causing a currently collocatable OOI to fall outside of the borders of the FOI, will be considered collocatable, while an OOI either falling outside of the borders of the dynamically movable FOI or causing a currently collocatable to fall outside of the borders of the FOI, will be considered non-collocatable. The later method is preferred over the former, since it will generally allow more OOIs to be collocated within a given FOI.

A FOI can be conveniently centered over a group of collocatable OOIs (either or both IOOIs and COOIs) by using an expandable bounding box. Specifically, and with reference to FIGS. 5-8, the use of an expandable bounding box 150 to iteratively determine whether FOIs are collocatable is described. First, the bounding box 150, which will start off as a point, will be initialized by making the x-y coordinates of the bounding box 150 equal to the coordinates of the initial OOI (shown as $OOI_0$ in FIG. 6) (action block 160). The next OOI (shown as $OOI_1$ in FIG. 6) is identified as the current OOI (action block 162), and the bounding box 150 is then expanded to include the current OOI (action block 164).

Significantly, only the sides of the bounding box 150 necessary to include the current OOI are expanded. In other words, if the x-coordinate of the current OOI is less than the minimum x coordinate of the bounding box 150, the left side of the bounding box 150 will be expanded, such that the minimum x-coordinate of the bounding box 150 matches the x-coordinate of the current OOI. Similarly, if the y-coordinate of the current OOI is less than the minimum y-coordinate of the bounding box 150, the bottom side of the bounding box 150 will be expanded, such that the minimum y-coordinate of the bounding box 150 matches the y-coordinate of the current OOI. If the x-coordinate of the current OOI is greater than the maximum x-coordinate of the bounding box 150, the right side of the bounding box 150 will be expanded, such that the maximum x-coordinate of the bounding box 150 matches the x-coordinate of the current OOI. If the y-coordinate of the current OOI is greater than the maximum y-coordinate of the bounding box 150, the top side of the bounding box 150 will be expanded, such that the maximum y-coordinate of the bounding box 150 matches the y-coordinate of the current OOI.

Figure 6:
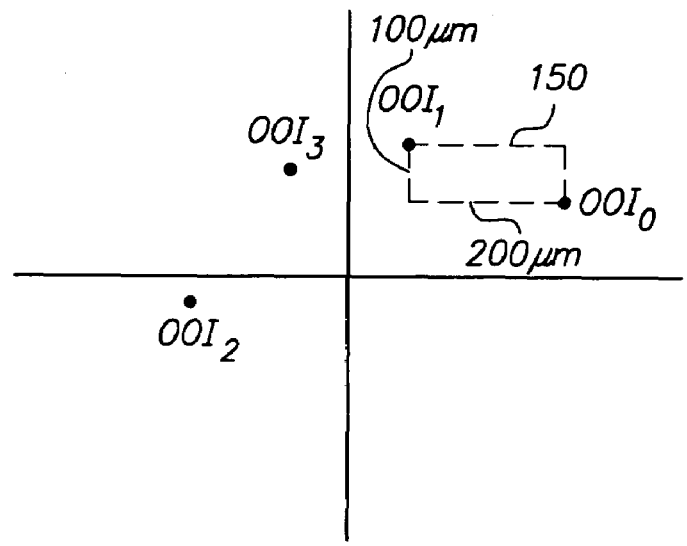
FIG. 6 is a diagram of a boundary box expanded to include an OOI.

In the exemplary case illustrated in FIG. 6, the x-coordinate of $OOI_1$ is less than the minimum x-coordinate of the bounding box 150 (which is essentially a point), and thus the left side of the bounding box 150 is expanded outward, so that the minimum x-coordinate of the bounding box 150 matches the x-coordinate of $OOI_1$. The y-coordinate of $OOI_1$ is also greater than the maximum y-coordinate of the bounding box 150, and thus the top side of the bounding box 150 is expanded outward, so that the maximum y-coordinate of the bounding box 150 matches the y-coordinate of $OOI_1$.

A determination is then made as to whether any dimension of the bounding box 150, after expansion, exceeds a dimension of the current FOI (decision block 166). If not, the current OOI is identified as being collocatable (action block 168), and the expanded boundary box will be set as the new boundary box for the next iteration (action block 172). In contrast, if the bounding box 150, after expansion, exceeds the dimensions of the current FOI, the current OOI is identified as being non-collocatable (action block 170), and the expanded boundary box will revert back to the previous boundary box (i.e., the previous boundary box will remain the new boundary box for the next iteration) (action block 174). In the exemplary case, the dimension of the boundary box, when expanded to include $OOI_1$, is 200 μm×100 μm. Assuming that the FOI has a predefined dimension of 400 μm×400 μm, both dimensions of the boundary box are less than the dimensions of the current FOI, and thus, $OOI_1$ will be identified as being collocatable, and the expanded boundary box will be set as the new boundary box for the next iteration.

Figure 7:
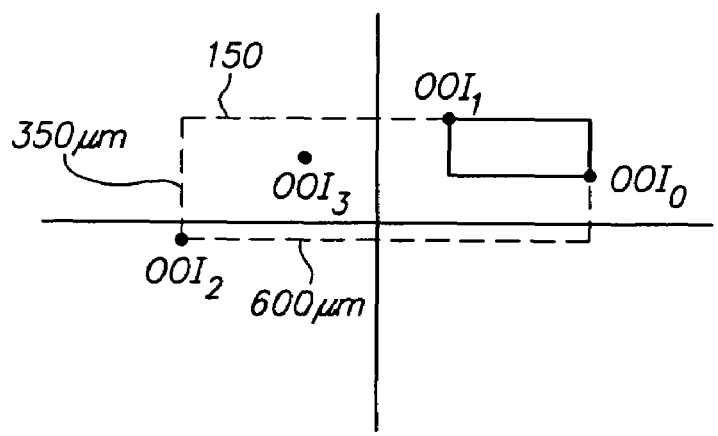
FIG. 7 is a diagram of the boundary box of FIG. 6 expanded to include another OOI.

A determination is then made as to whether the current OOI is the last OOI assigned to the FOI (decision block 176). If so, the process ends (action block 178). If not, the process will then return to action block 162 in order to determine if the next OOI (shown as $OOI_2$ in FIG. 7) is collocatable. For example, in the exemplary case illustrated in FIG. 7, the x-coordinate of $OOI_2$ is less than the minimum x-coordinate of the new bounding box 150, and thus the left side of the bounding box 150 is expanded outward, so that the minimum x-coordinate of the bounding box 150 matches the x-coordinate of $OOI_2$. The y-coordinate of $OOI_2$ is less than the minimum y-coordinate of the bounding box 150, and thus the bottom side of the new bounding box 150 is expanded outward, so that the minimum y-coordinate of the bounding box 150 matches the y-coordinate of $OOI_2$. As illustrated in FIG. 7, the dimension of the new boundary box, when expanded to include $OOI_2$, is 600 μm×350 μm. In this case, the x-dimension of the boundary box is greater than the x-dimension of the current FOI. Thus, $OOI_2$ will be identified as being non-collocatable, and the previous boundary box will remain the new boundary box for the next iteration.

Figure 8:
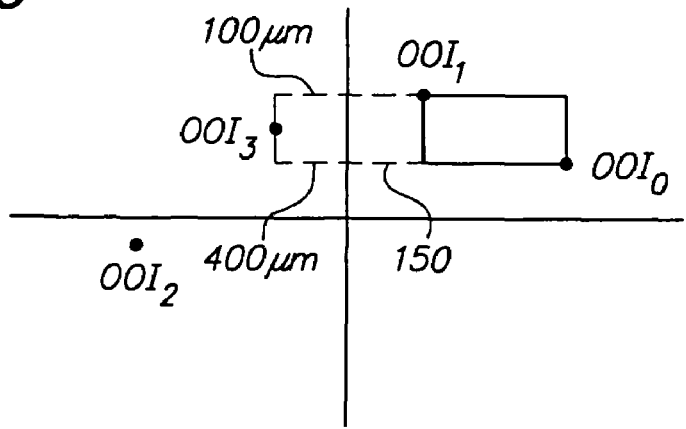
FIG. 8 is a diagram of the boundary box of FIG. 6 expanded to include still another OOI.

In the exemplary case illustrated in FIG. 8, the next OOI is shown as $OOI_3$. The x-coordinate of $OOI_3$ is greater than the maximum x-coordinate of the new bounding box 150, and thus the right side of the bounding box 150 is expanded outward, so that the maximum x-coordinate of the bounding box 150 matches the x-coordinate of $OOI_3$. As illustrated in FIG. 8, the dimension of the new boundary box, when expanded to include $OOI_3$, is 300 μm×100 μm. In this case, both dimensions of the boundary box are less than the dimensions of the current FOI, and thus, $OOI_3$ will be identified as being collocatable, and the expanded boundary box will be set as the new boundary box for the next iteration. It should be noted that, once the bounding box has been finally set, the FOI processor 32 can easily center the FOI over the collocated OOIs by assigning an x-coordinate to the FOI equal to the average of the minimum and maximum x-coordinates of the bounding box 150, and likewise assigning a y-coordinate to the FOI equal to the average of the minimum and maximum y-coordinates of the bounding box 150.

After all 22 FOIs have been generated, the FOI processor 32 stores the x-y coordinates of all of the FOIs in memory 36 for later use by the routing processor 34. Specifically, the routing processor 34 maps the x-y coordinates of the FOIs using a suitable routing algorithm, such as a modified "traveling salesman" algorithm, which determines the most efficient viewing route for presenting the FOIs in the reviewing station 22. The routing processor 34 then stores the x-y coordinates of the FOIs, along with the routing plan (which in the illustrated embodiment, is accomplished by simply placing the FOIs in a list in the order that they will be reviewed), in memory 36 for subsequent access by the reviewing station 22.

Referring back to FIG. 2, in one preferred embodiment, a total of three reviewing stations 20 are shown coupled to the server 22, so that up to three cytotechnologists have simultaneous access to the pertinent information stored in the server 20. Notably, the system 10 can typically process the slides 14 much quicker than a cytotechnologist can review them. Even if the specimen processing speed of the system 10 is slower than the specimen review speed of a cytotechnologist, the system 10 can generally be operated 24 hours a day, whereas the typical cytotechnologist will only work 8 hours a day. Thus, the bottleneck in the screening process occurs at the human level, i.e., the detailed review of the biological material contained on the slides 14. Thus, it can be appreciated that the use of multiple reviewing stations 22 alleviates this bottleneck, thereby providing for a much more efficient process.

Before discussing the details of the reviewing stations 22, reference is made to FIG. 3, which illustrates an exemplary FOV that each reviewing station centers over a FOI. In the illustrated embodiment, the FOV has a diameter of 2.2 mm, and the FOI is defined by a 0.4 mm×0.4 mm square circumscribed by the FOV. In the actual embodiment, the borders of the FOI are imaginary and cannot be seen, so that the cytotechnologist's view of any OOIs is not obstructed. In order to more quickly direct the cytotechnologist's attention to the FOI and to provide a reference that generally indicates the exact region bound by the imaginary borders of the FOI, an L-shaped mark indicator 152 is provided. The mark indicator 152 captures the FOI (i.e., an open square portion 154 of the mark indicator 152 borders the left and bottom sides of the FOI). A 0.05 mm margin is provided between the mark indicator 152 borders and the imaginary borders of the FOI, so that the portions of OOIs extending outside of the left and bottom borders of the FOI (resulting from an OOI that is included within the FOI, but centered near the left or bottom border of the FOI) will not be obstructed by the mark indicator 152. The mark indicator 152 also serves to provide a means for the cytotechnologist to electronically mark the FOI (e.g., by pushing a button that electronically colors the mark indicator 152) as requiring further review by a pathologist (e.g., if an OOI has malignant or pre-malignant attributes).

Referring back to FIG. 2, each reviewing station 22 comprises a microscope 38 and a motorized stage 40. The slide 14 (after image processing) is mounted on the motorized stage 40, which moves the slide 14 relative to the viewing region of the microscope 38 based on the routing plan and a transformation of the x-y coordinates of the FOIs obtained from memory 36. Specifically, these x-y coordinates, which were acquired relative to the x-y coordinate system of the imaging station 18, will be transformed into the x-y coordinate system of the reviewing station 22 using the fiducial marks 16 affixed to the slide 14 (shown in FIG. 1). Thus, it is ensured that the x-y coordinates of the slide 14 during the reviewing process are correlated to the x-y coordinates of the slide 14 during the imaging process. The motorized stage 40 will then move in accordance with the transformed x-y coordinates of the FOIs, as dictated by the routing plan.

In the illustrated embodiment, to advance from one FOI to another, the cytotechnologist presses an activation switch (not shown). In this sense, the reviewing station 22 is semi-automatic. Alternatively, the FOIs are automatically advanced from one to the next. In this case, the motorized stage 40 may optionally pause for a predetermined amount of time for each FOI. In this sense, the reviewing station 22 is fully automatic.

As the selected FOIs are presented in the FOV of the microscope 38, the cytotechnologist reviews the FOIs and makes decisions about the level of cell abnormality, if any. The cytotechnologist will electronically mark any FOIs that are suspect. The cytotechnologist is capable of returning to a previously viewed FOI, and manually moving to (and viewing) locations on the slide not encompassed by FOIs. Following review of the slide 14, if any FOIs have been marked by the cytotechnologist, the reviewing station 22 preferably automatically scans the entire biological specimen 12, so that 100% viewing coverage is ensured. The cytotechnologist is able to pause the autoscan and to move the stage 40 in order to reposition and access locations on the slide 14, as desired.

Although particular embodiments of the present invention have been shown and described, it should be understood that the above discussion is not intended to limit the invention to these embodiments. Those skilled in the art will appreciate that various changes and modifications may be made to the above-described embodiments without departing from the invention, as defined by the appended claims.

What is claimed:

1. A processor-controlled system configured for grouping objects of interest (OOIs) located on a microscope slide within fields of interest (FOIs) covering portions of the slide, including for each FOI:

sequentially selecting OOIs that have not been assigned to any FOI;

assigning an initially selected OOI to the each FOI;

determining if each subsequently selected OOI can be collocated with OOIs previously assigned to the each FOI by initially defining a current boundary that includes the initially selected OOI, wherein the boundary is geometrically similar to the each FOI, and for each subsequently selected OOI, expanding the current boundary to include the subsequently selected OOI, and if each dimension of the expanded boundary is the same or smaller than a corresponding dimension of the each FOI, identifying the subsequently selected OOI as a collocatable OOI and setting the expanded boundary as a new current boundary;

assigning each collocatable OOI to the each FOI; and outputting the locations of the FOIs to which the collocatable OOIs have been assigned in a user-readable format.

2. The system of claim 1, wherein the FOIs have predetermined dimensions.

3. The system of claim 1, wherein the number of FOIs is fixed.

4. The system of claim 1, wherein the system is configured to center each FOI over an initially assigned OOI.

5. The system of claim 1, wherein the system is configured to center each FOI over a group of collocated OOIs.

6. The system of claim 1, wherein the OOIs are ranked, and the OOIs are selected in accordance with the ranking of the OOIs.

7. The system of claim 6, wherein the OOIs are cells.

8. The system of claim 7, wherein the cells are ranked in accordance with a likelihood that the cells are at risk for having an abnormal condition.

9. The system of claim 8, wherein the abnormal condition is malignancy or pre-malignancy.

10. The system of claim 1, wherein the FOIs are divided into first and second FOIs, and the OOIs are divided into first and second OOIs, and wherein the system is further configured for grouping the first OOIs within the first FOIs, and grouping the second OOIs within the second FOIs, including for each first FOI:
sequentially selecting first OOIs that have not been assigned to any first FOI;
assigning an initially selected first OOI to the each first FOI;
determining if each subsequently selected first OOI can be collocated with first OOIs previously assigned to the each first FOI;
identifying each subsequently selected first OOI as a collocatable first OOI based on the determination; and
assigning each first collocatable OOI to the each first FOI; and
for each second FOI:
sequentially selecting second OOIs that have not been assigned to any second FOI;
assigning an initially selected second OOI to the each second FOI;
determining if each subsequently selected second OOI can be collocated with second OOIs previously assigned to the each second FOI;
identifying each subsequently selected second OOI as a collocatable second OOI based on the determination; and
assigning each second collocatable OOI to the each second FOI.

11. The system of claim 10, wherein grouping the first OOIs within the first FOIs, and grouping the second OOIs within the second FOIs further includes for each first FOI:
sequentially selecting second OOIs that have not been assigned to any first or second FOI, the second OOIs being selected after the first OOIs;
determining if each subsequently selected second OOI can be collocated with first or second OOIs previously assigned to the each first FOI;
identifying each selected second OOI as a second collocatable OOI based on this determination; and
assigning each second collocatable OOI to the each first FOI.

12. The system of claim 10, wherein grouping the first OOIs within the first FOIs, and grouping the second OOIs within the second FOIs further includes for each second FOI:
sequentially selecting first OOIs that have not been assigned to any first or second FOI, the first OOIs being selected after the second OOIs;
determining if each subsequently selected first OOI can be collocated with first or second OOIs previously assigned to the each second FOI;
identifying each selected first OOI as a first collocatable OOI based on the determination; and
assigning each first collocatable OOI to the each second FOI.

13. The system of claim 10, wherein the first OOIs are individual cells, and the second OOIs are cell clusters.

14. A method of presenting objects of interest (OOIs) located on a microscope slide within fields of interest (FOIs) covering portions of the slide using a microscope with a field of view (FOV) that is displayed to a user, comprising for each FOI:
using a processor for sequentially selecting OOIs that have not been assigned to any FOI;
assigning an initially selected OOI to the FOI;
determining if each subsequently selected OOI can be collocated with OOIs previously assigned to the each FOI by initially defining a current boundary that includes the initially selected OOI, wherein the boundary is geometrically similar to the each FOI, and for each subsequently selected OOI, expanding the current boundary to include the subsequently selected OOI, and if each dimension of the expanded boundary is the same or smaller than a corresponding dimension of the each FOI, identifying the subsequently selected OOI as a collocatable OOI and setting the expanded boundary as a new current boundary;
assigning each collocatable OOI to the each FOI; and
automatically or semi-automatically moving the user displayed FOV to encompass the each FOI.

15. The method of claim 14, wherein the FOIs have predetermined dimensions.

16. The method of claim 14, wherein the number of FOIs is fixed.

17. The method of claim 14, further comprising centering each FOI over an initially assigned OOI.

18. The method of claim 14, further comprising centering each FOI over a group of collocated OOIs.

19. The method of claim 14, wherein the OOIs are ranked, and the OOIs are selected in accordance with the ranking of the 00 Is.

20. The method of claim 19, wherein the OOIs are cells.

21. The method of claim 20, wherein the cells are ranked in accordance with a likelihood that the cells are at risk of having an abnormal condition.

22. The method of claim 21, wherein the abnormal condition is malignancy or pre-malignancy.

23. The method of claim 14, wherein the FOIs are divided into first and second FOIs, and the OOIs are divided into first and second OOIs, wherein the method is further for grouping first OOIs within first FOIs, and for grouping second OOIs within second FOIs, the method further comprising:
for each first FOI:
sequentially selecting first OOIs that have not been assigned to any first FOI;
assigning an initially selected first OOI to the each first FOI;
determining if each subsequently selected first OOI can be collocated with first OOIs previously assigned to the each first FOI;
identifying each subsequently selected first OOI as a collocatable first OOI based on the determination; and
assigning each first collocatable OOI to the each first FOI; and
for each second FOI:

sequentially selecting second OOIs that have not been assigned to any second FOI;

assigning an initially selected second OOI to the each second FOI;

determining if each subsequently selected second OOI can be collocated with second OOIs previously assigned to the each second FOI;

identifying each subsequently selected second OOI as a collocatable second OOI based on the determination; and assigning each second collocatable OOI to the each second FOI.

24. The method of claim 23, further comprising for each first FOI:

sequentially selecting second OOIs that have not been assigned to any first or second FOI, the second OOIs being selected after the first OOIs;

determining if each subsequently selected second OOI can be collocated with first or second OOIs previously assigned to the each first FOI;

identifying each selected second OOI as a second collocatable OOI based on this determination; and assigning each second collocatable OOI to the each first FOI.

25. The method of claim 23, further comprising for each second FOI:

sequentially selecting first OOIs that have not been assigned to any first or second FOI, the first OOIs being selected after the second OOIs;

determining if each subsequently selected first OOI can be collocated with first or second OOIs previously assigned to the each second FOI;

identifying each selected first OOI as a first collocatable OOI based on the determination; and assigning each first collocatable OOI to the each second FOI.

26. The method of claim 23, wherein the first OOIs are individual cells, and the second OOIs are cell clusters.

27. The system of claim 1, wherein the system is configured to define a location of the each FOI based on locations of all of the collocatable OOIs.

28. The system of claim 27, wherein the location of the each FOI is defined to include all of the collocatable OOIs.

29. The method of claim 14, further comprising defining a location of the each FOI based on locations of all of the collocatable OOIs.

30. The method of claim 29, wherein the location of the each FOI is defined to include all of the collocatable OOIs.

* * * * *

UNITED STATES PATENT AND TRADEMARK OFFICE
CERTIFICATE OF CORRECTION

PATENT NO. : 7,590,492 B2 Page 1 of 1
APPLICATION NO. : 10/866397
DATED : September 15, 2009
INVENTOR(S) : Zahniser et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1098 days.

Signed and Sealed this

Twenty-first Day of September, 2010

David J. Kappos
*Director of the United States Patent and Trademark Office*